(12) United States Patent
Xu et al.

(10) Patent No.: US 8,545,685 B2
(45) Date of Patent: Oct. 1, 2013

(54) CLEANING PROCESS OF PRODUCING LACTIC ACID

(75) Inventors: Nanping Xu, Jiangsu (CN); Weixing Li, Jiangsu (CN); Weihong Xing, Jiangsu (CN); Yiqun Fan, Jiangsu (CN)

(73) Assignee: Nanjing University of Technology (CN)

( * ) Notice: Subject to any disclaimer, the term of this patent is extended or adjusted under 35 U.S.C. 154(b) by 80 days.

(21) Appl. No.: 13/127,307

(22) PCT Filed: Apr. 20, 2009

(86) PCT No.: PCT/CN2009/000418
§ 371 (c)(1),
(2), (4) Date: May 3, 2011

(87) PCT Pub. No.: WO2010/051676
PCT Pub. Date: May 14, 2010

(65) Prior Publication Data
US 2011/0210001 A1    Sep. 1, 2011

(30) Foreign Application Priority Data
Nov. 10, 2008 (CN) .......................... 2008 1 0195297

(51) Int. Cl.
*B01D 61/42* (2006.01)
*B01D 61/58* (2006.01)

(52) U.S. Cl.
USPC ........... 204/430; 204/531; 204/534; 204/537; 204/538

(58) Field of Classification Search
USPC .......................... 204/430, 531, 534, 537, 538
See application file for complete search history.

(56) References Cited

U.S. PATENT DOCUMENTS 3,619,397 A    11/1971    Jacquemet
5,002,881 A *   3/1991    Van Nispen et al. .......... 435/139

(Continued)

FOREIGN PATENT DOCUMENTS

CN    1031112 A    2/1989
CN    1730457 A    2/2006

(Continued)

OTHER PUBLICATIONS

Zhang R.Q. The application of the technic of membrane separation in producing L-lactic acid, Hebei Chemical Industry, Feb. 2008, vol. 31, No. 2, pp. 35-36.

(Continued)

*Primary Examiner* — Arun S Phasge
(74) *Attorney, Agent, or Firm* — Schmeiser, Olsen & Watts LLP

(57) ABSTRACT

Provided is a cleaning process of producing lactic acid. Firstly saccharification liquid is prepared through saccharated materials, then fermented with nutritive materials and lactic acid bacteria, and liquid alkali is used to adjust the pH. The fermentation broth is filtrated with porous membrane, and the lactic acid bacteria in the interception liquid are then reintroduced into the porous membrane for recycling. The permeate from porous membrane is subjected to nanofiltration to be decolored and purified. The concentrated solution from nanofiltration and the cleaning liquid from fermentation tank and its affiliated equipment are filtrated and sterilized by using ceramic membrane, and then are reintroduced into the fermentation unit for recycling. The permeate from nanofiltration is then subjected to bipolar electrodialysis system to prepare lactic acid, and the liquid alkali produced at the same time is reintroduced into the fermentation tank for recycling. The lactic acid is finally concentrated by using vacuum distillation. The process recycles the bacteria in the liquid alkali and matured fermentation broth, and is characterized by low material consumption and emission, low pollution, reduced cost and cleanness and environmentally protection of the whole production process.

9 Claims, 1 Drawing Sheet

(56) References Cited

U.S. PATENT DOCUMENTS

| | | | |
|---|---|---|---|
| 5,503,750 A * | 4/1996 | Russo et al. | 210/641 |
| 6,319,382 B1 | 11/2001 | Norddahl | |
| 2004/0033573 A1* | 2/2004 | Norddahl et al. | 435/139 |

FOREIGN PATENT DOCUMENTS

| | | |
|---|---|---|
| CN | 101225413 A | 7/2008 |
| CN | 101234962 A | 8/2008 |
| CN | 101265179 A | 9/2008 |
| CN | 101294169 A | 10/2008 |
| CN | 101294174 A | 10/2008 |
| WO | 2004057008 | 7/2004 |

OTHER PUBLICATIONS

GB2023-2003—National Standards for Food Additives, lactic acid (GB); ICS 67.220.20; Dec. 1, 2001, 11 pages total.

* cited by examiner

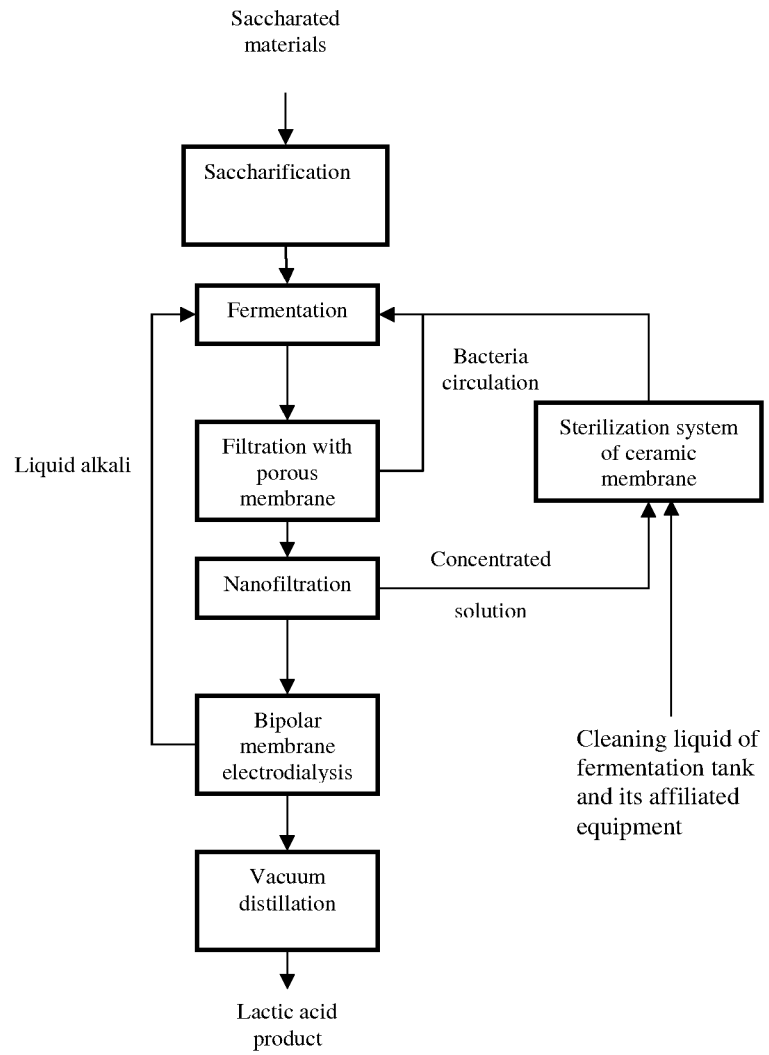

CLEANING PROCESS OF PRODUCING LACTIC ACID

FIELD OF TECHNOLOGY

The present invention relates to a cleaning process of producing lactic acid. More particularly, this invention relates to a process of producing lactic acid by using integrated membrane process for lactic acid extraction and recycling of fermentation bacteria and water for fermentation.

BACKGROUND

Lactic acid has been widely used in chemical, foodstuff and pharmaceutical industries. And more particularly, polylactic acid (PLA) will become an important substitute product for the petrochemical resources. With the improvement of the living standards, people have growing demands for resources, such as packaging materials (food boxes, food bags, agricultural plastics, etc.). According to statistics, the production only of the plastics and chemical fibers in the world has reached over 32 million ton/year at present. However, as the petroleum resources will gradually die out, some new renewable resources will become main substitute products, and polylactic acid is one of them. At present, PLA products (lunch boxes, medical appliances, etc.) have already been in popularization and application. Therefore, development and utilization of lactic acid as a renewal resource is of great significance, with broad market prospects.

In industry, lactic acid is mainly produced by the method of fermentation, using starch products as raw materials and subject to bacteria or rhizopus fermentation, i.e. fermentation→calcium salt neutralization→acid hydrolysis→lactic acid product. In the process, a great deal of calcium sulphate waste residue, waste water and carbon dioxide produce, causing serious environmental problems.

In order to reduce preparation costs and improve production quality of lactic acid, about it is reported at home and abroad about application of electrodialysis as the technology for extraction of fermentation broth. In the US patent "Process for the Purification of Lactic Acid" (U.S. Pat. No. 3,619,397) in 1971, there is descried a lactic acid extraction technology by firstly conducting solvent extraction and then employing electrodialysis with usual anionic membranes and cationic membrane stack. Toxic amine materials are generally used as the solvent for lactic acid extraction, which tends to cause secondary pollution to the product of lactic acid. In the Chinese patent "Extraction Process and Equipment for Lactic Acid Electrodialysis" (ZL 87104858.2), there is described calcium lactate extraction by electrodialysis composed of usual anionic membrane and cationic membrane stack, with conversion rate of 85%. However, this process still uses the method of calcium salt fermentation. Although calcium ions finally do not form calcium sulphate deposition, it will be discharged in other forms, causing serious environmental pollution. Denmark Plougmann, Vingtoft & Partners A/S has reported "Production of lactic acid from whey proteins where electrodialysis causes less biofouling of the electrodialysis membrane" (NZ336852), and has applied for patent protection of "Fermentative Production and Isolation of Lactic Acid" (ZL 97181922.X) in China. This invention applies a method of adding ammonia for formation of ammonium lactate, and isolating lactic acid by a process comprising ultra filtration, ion exchange, conventional electrodialysis and electrodialysis with bipolar membranes. This process causes certain environmental pollution due to severe volatilization. As all the above several methods do not practice comprehensive recycling of water for fermentation or discharge water, it is difficult to achieve high efficient utilization of water resources. Therefore, the cleaning process for lactic acid production has become the focus for domestic and foreign researches.

SUMMARY

An aspect relates to a novel cleaning process of producing lactic acid for surmounting some shortcomings of the existing processes for lactic acid production, such as excessive discharge of waste water and waste residues and high material consumption.

The technical scheme of the present invention is: A cleaning process of producing lactic acid, wherein saccharification liquid is firstly prepared through saccharated materials, then fermented with nutritive materials and lactic acid bacteria, and liquid alkali is used to adjust the pH. The fermentation broth is filtrated with porous membrane, and the lactic acid bacteria in the interception liquid are then reintroduced into the porous membrane for recycling. The permeate from porous membrane is subjected to nanofiltration to be decoloured and purified. The concentrated solution from nanofiltration and the cleaning liquid from fermentation tank and its affiliated equipment are filtrated and sterilized by using ceramic membrane, and then are reintroduced into the fermentation unit for recycling. The permeate from nanofiltration is then subjected to bipolar electrodialysis system to prepare lactic acid, and the liquid alkali produced at the same time is reintroduced into the fermentation tank for recycling. The lactic acid is finally concentrated by using vacuum distillation.

The specific process flow includes:

(1) Preparation of saccharification liquid: Saccharated materials are crushed and dissolved in water, and solid impurities (if any) are filtrated.

(2) Fermentation of saccharification liquid: The prepared saccharification liquid is added into the fermentation tank, and at the same time, fermented with nutritive materials and lactic acid bacteria under certain temperature and pH conditions. In order to regulate pH of the system, liquid alkali is continuously added by the means of automatic control.

(3) Filtration of fermentation broth with porous membrane and recycling of bacteria: When the mass percentage concentration of sugar content of the system is fermented to be lower than 0.5%, the fermentation broth is pumped into the porous membrane unit, and after it is filtrated with the porous membrane, bacteria, macromolecular proteins and polysaccharide materials in the system will be intercepted and reintroduced into the fermentation unit. The permeate is the monovalent salt solution containing lactic acid.

(4) Nanofiltration for decolour and removal of divalent ions: The permeate from porous membrane is fed into the nanofiltration unit, and ions above divalent of the system such as coloring matter, saccharide, calcium, magnesium and zinc are intercepted by the nanofiltration membrane and reintroduced into the fermentation unit as nutritive materials and necessary microelements for recycling. But they must first enter into the ceramic membrane system like the cleaning liquid of fermentation tank and its affiliated equipment for removal of hybrid bacteria. The permeate from nanofiltration is relatively pure monovalent lactate salt solution.

(5) Separation of lactate salt with bipolar membrane electrodialysis and preparation of lactic acid and liquid alkali: The permeate from nanofiltration is fed into the bipolar membrane unit, and under the action of DC electric field, lactate salt is decomposed into lactic acid and liquid alkali. Then lactic acid is fed into the following procedures, and liquid alkali is reintroduced into the fermentation unit as pH regulator.

(6) The lactic acid solution coming from the bipolar membrane unit is fed into the vacuum distillation unit and dehydrated appropriately water content for preparation of lactic acid product of corresponding specifications.

The said saccharated materials refer to saccharatid crops, preferably corn, wheat, yam, potato, molasses or plant fiber. Among them, corn, wheat, yam, potato and plant fiber shall be crushed at first, and then hydrolyzed with addition of amylases, molasses are directly hydrolyzed. The said prepared saccharification liquid is aqueous solution with mass percentage concentration of glucose being 10~30%

The said nutritive materials refer to are soybean meal hydrolysate, bran or corn steep liquor. The addition amount of nutritive materials (dry weight) is 0.1~40% of total mass of saccharification liquid. The said lactic acid bacteria is *L. delbrueckii*, and its addition amount is 5~20% of total volume of saccharification liquid, fermentation temperature is 45~60° C. and pH is 5~7.

The said liquid alkali refers to aqueous solution containing hydrate with monovalent cation, preferably sodium hydroxide, potassium hydroxide or ammonium hydroxide, and mass percentage concentration of liquid alkali is 5%~30%.

The said porous membrane is ceramic membrane, metallic membrane or organic membrane, and the pore size of porous membrane is 5 nm~15 μm. The ceramic membrane is preferred, and the preferred pore size is 20 nm~500 nm.

The fermentation broth is initially filtrated with the said porous membrane, with operation pressure being 0.01~0.5 MPa and flow velocity of membrane surface being 0.01~5 m/s. The permeate from porous membrane is subjected to the said nanofiltration for decoloring and purification, with operating pressure being 0.5~2.5 MPa.

The said sterilization system of ceramic membrane is an operation unit employing ceramic membrane with pore size of 20 nm~100 nm to remove hybrid bacteria from the feed. In the operation unit, flow velocity of ceramic filtration membrane surface is 0.01~3 m/s and cycle of concentration is 8~10.

The operating current density of the said bipolar electrodialysis system is 30~300 A/m$^2$, and the mass percentage concentration of lactate salt in the permeate from nanofiltration introduced into the bipolar electrodialysis system is 10~40%.

The bipolar electrodialyser employed in the said bipolar electrodialysis process is composite membrane stack structure of two or three compartments.

The cleaning process of producing lactic acid employed by the present invention for extracting fermentation broth with liquid alkali neutralization fermentation and membrane integration technologies exhibits magnificent advantages:

(1) Compared with conventional calcium salt fermentation, the present invention is characterized by small pollution and low material consumption. In the conventional calcium salt fermentation, lactic acid is mainly prepared by firstly adding calcium carbonate into fermentation system for neutralizing acidity of the system, and then using strong sulfuric acid to decompose lactic acid calcium. Large amount of calcium sulphate waste residues and carbon dioxide produce in the process of the method, causing relatively serious environmental problems. However, in the present invention, liquid alkali is used for neutralization, and lactic acid and corresponding liquid alkali are prepared finally through bipolar electrodialysis, and the liquid alkali of this part can be recycled. As a result, production of waste residue and carbon dioxide is inhibited, without use of calcium carbonate and sulfuric acid (2) The present invention realizes bacterial recycling fermentation, saving inoculation amount and reducing fermentation costs. Fermentation broth is filtrated with porous membrane, and the bacteria in the interception liquid is intercepted and then reintroduced into the porous membrane for recycling, dramatically reducing bacteria inoculation amount of fermentation broth and lowering fermentation costs.

(3) The present invention designs a unique sterilization system of ceramic membrane, dramatically reducing fermentation water consumption. Ceramic membrane technology is used for purifying and sterilizing cleaning liquid of fermentation tank and nanofiltration concentrated solution and realizing recycling, resolving the difficult problem of original high water consumption of fermentation factories. It is a novel clean process of producing lactic acid with extremely low emission.

(4) The present invention employs advanced integrated technology of porous membrane, nanofiltration and bipolar electrodialysis, improving quality of lactic acid product. The conventional calcium salt method mainly uses plate or belt filtration for solid-liquid separation. Its precision is far lower than that of porous membrane and nanofiltration membrane, and removal effect of such macromolecules as coloring matter is poor, finally affecting product quality. In the present invention, integrated technology of multiple types of membranes are adopted for separating and purifying lactic acid fermentation broth, and lactic acid separated and prepared through bipolar electrodialysis is relatively higher in purity than that prepared with conventional method.

BRIEF DESCRIPTION OF THE DRAWING

FIG. 1 is the block diagram of the cleaning process of producing lactic acid.

DETAILED DESCRIPTION

The invention will be further described with reference to the embodiments.

Embodiment 1

As indicated in FIG. 1, the steps of making the present invention are as follows:

(1) Corns are crushed, and then heated and dissolved in water, solid granulates are removed by rotary drum filter, and 10L saccharification liquid with mass percentage concentration of glucose of 15% is prepared with addition of saccharifying enzyme into the filtered liquid.

(2) The prepared saccharification liquid is fed into saccharification tank and fermented at the temperature of 45° C. by adding soybean meal hydrolysate with mass percentage (dry weight) of 2% and *L. delbrueckii* with volume of saccharification liquid of 7%. Sodium hydroxide solution with mass percentage concentration of 20% is continuously added by means of automatic control to adjust pH of the system and maintain pH at 6.8.

(3) When mass percentage concentration of sugar content of the fermentation system is lower than 0.5%, the fermentation broth is pumped into ceramic fermentation unit. The pore size of employed ceramic membrane is 50 nm, operating pressure of unit is 0.2 MPa, flow velocity of membrane surface is 3 m/s, permeate flux of ceramic membrane is 80 L·m$^{-2}$·h$^{-1}$, volume of permeate from ceramic membrane unit accounts for 75% of the total volume, and the remaining 25% of fermentation interception liquid containing bacteria is reintroduced into the fermentation unit as supplement of fermentation bacteria. The permeate is lactic acid sodium solution with mass percentage concentration of 10%.

(4) The permeate from ceramic membrane (i.e. lactic acid sodium solution with mass percentage concentration of 10%) is boosted to 1.0 MPa and then pumped into nanofiltration unit. Nanofiltration membrane employed is DK nanofiltration membrane of GE Corporation. The permeate from ceramic membrane accounts for 80% of the volume of the feed, and the remaining 20% is fed into sterilization system of ceramic membrane, pore size of ceramic membrane is 50 nm. At this time, permeate from nanofiltration is relatively purified lactic acid sodium solution. Meanwhile, the sterilization system of ceramic membrane can also treat the cleaning liquid of fermentation tank and its affiliated equipment, and remove hybrid bacteria, thus allowing water to reintroduce into the fermentation unit for recycling. Flow velocity of ceramic filtration membrane surface of this unit is 0.05 m/s and cycle of concentration is 10.

(5) The permeate from nanofiltration is passed into the bipolar electrodialysis unit, the employed bipolar electrodialyser is a two-compartment structure composed of repeated stack of cationic membranes and bipolar membranes; both sides of membrane stack are electrified with direct current whose density is 100 A/m$^2$, and lactic acid sodium is decomposed into lactic acid and sodium hydroxide. Among them, sodium hydroxide coming from cationic compartment is reintroduced into fermentation unit for regulating pH, and lactic acid solution with mass percentage concentration of 12% comes from bipolar membrane compartment.

(6) Lactic acid solution issuing from bipolar membrane compartment is fed into vacuum distillation unit, and dehydrated to obtain lactic acid product with mass percentage concentration of 85%, whose quality meet the standard of GB2023-2003.

Embodiment 2

As indicated in FIG. 1, the steps of making the present invention are as follows:

(1) Corns are crushed, and then heated and dissolved in water, solid granulates are removed by rotary drum filter, and 10L saccharification liquid with mass percentage concentration of glucose of 20% is prepared with addition of saccharifying enzyme into the filtered liquid.

(2) The prepared saccharification liquid is fed into saccharification tank and fermented at the temperature of 50° C. by adding corn steep liquor with mass percentage (dry weight) of 3% and *L. delbrueckii* with volume of saccharification liquid of 8%. Sodium hydroxide solution with mass percentage concentration of 30% is continuously added by means of automatic control to adjust pH of the system and maintain pH at 6.8.

(3) When mass percentage concentration of sugar content of the fermentation system is lower than 1%, the fermentation broth is pumped into stainless steel fermentation unit. The pore size of employed stainless steel membrane is 200 nm, operating pressure of unit is 0.15 MPa, flow velocity of membrane surface is 4 m/s, permeate flux of ceramic membrane is 100 L·m$^{-2}$·h$^{-1}$, volume of permeate from ceramic membrane unit accounts for 80% of the total volume, and the remaining 20% of fermentation interception liquid containing bacteria is reintroduced into the fermentation unit as supplement of fermentation bacteria. The permeate is lactic acid sodium solution with mass percentage concentration of 13%.

(4) The permeate from ceramic membrane (i.e. lactic acid sodium solution with mass percentage concentration of 13%) is boosted to 1.5 MPa and then pumped into nanofiltration unit. Nanofiltration membrane employed is DK nanofiltration membrane of GE Corporation. The permeate from ceramic membrane accounts for 75% of the volume of the feed, and the remaining 25% is fed into sterilization system of ceramic membrane, pore size of ceramic membrane is 20 nm. At this time, permeate from nanofiltration is relatively purified lactic acid sodium solution. Meanwhile, the sterilization system of ceramic membrane can also treat the cleaning liquid of fermentation tank and its affiliated equipment, and remove hybrid bacteria, thus allowing water to reintroduce into the fermentation unit for recycling. Flow velocity of ceramic filtration membrane surface of this unit is 0.5 m/s and cycle of concentration is 9.

(5) The permeate from nanofiltration is passed into the bipolar electrodialysis unit, the employed bipolar electrodialyser is a two-compartment structure composed of repeated stack of cationic membrane and bipolar membrane; both sides of membrane stack are electrified with direct current whose density is 120 A/m$^2$, and lactic acid sodium is decomposed into lactic acid and sodium hydroxide. Among them, sodium hydroxide coming from cationic compartment is reintroduced into fermentation unit for regulating pH, and lactic acid solution with mass percentage concentration of 13% comes from bipolar membrane compartment.

(6) Lactic acid solution issuing from bipolar membrane compartment is fed into vacuum distillation unit, and dehydrated to obtain lactic acid product with mass percentage concentration of 85%, whose quality meet the standard of GB2023-2003.

Embodiment 3

As indicated in FIG. 1, the steps of making the present invention are as follows:

(1) Corns are crushed, and then heated and dissolved in water, solid granulates are removed by rotary drum filter, and 10L saccharification liquid with mass percentage concentration of glucose of 10% is prepared with addition of saccharifying enzyme into the filtered liquid.

(2) The prepared saccharification liquid is fed into saccharification tank and fermented at the temperature of 48° C. by adding corn steep liquor and bran with mass percentage (dry weight) of 5% and *L. delbrueckii* with volume of saccharification liquid of 7%. Sodium hydroxide solution with mass percentage concentration of 15% is continuously added by means of automatic control to adjust pH of the system and maintain pH at 6.8.

(3) When mass percentage concentration of sugar content of the fermentation system is lower than 1%, the fermentation broth is pumped into PVC microfiltration fermentation unit. The pore size of employed PVC microfiltration membrane is 200 nm, operating pressure of unit is 0.1 MPa, flow velocity of membrane surface is 2 m/s, permeate flux of ceramic membrane is 40 L·m$^{-2}$·h$^{-1}$, volume of permeate from ceramic membrane unit accounts for 80% of the total volume, and the remaining 20% of fermentation interception liquid containing bacteria is reintroduced into the fermentation unit as supplement of fermentation bacteria. The permeate is lactic acid sodium solution with mass percentage concentration of 8%.

(4) The permeate from ceramic membrane (i.e. lactic acid sodium solution with mass percentage concentration of 8%) is boosted to 0.8 MPa and then pumped into nanofiltration unit. Nanofiltration membrane employed is Duracid nanofiltration membrane of KOCH Corporation. The permeate from ceramic membrane accounts for 70% of the volume of the feed, and the remaining 30% is fed into sterilization system of ceramic membrane, pore size of ceramic membrane is 20 nm. At this time, permeate from nanofiltration is relatively purified lactic acid sodium solution. Meanwhile, the sterilization system of ceramic membrane can also treat the cleaning liquid of fermentation tank and its affiliated equipment, and remove hybrid bacteria, thus allowing water to reintroduce into the fermentation unit for recycling. Flow velocity of ceramic filtration membrane surface of this unit is 1.5 m/s and cycle of concentration is 8.

(5) The permeate from nanofiltration is passed into the bipolar electrodialysis unit, the employed bipolar electrodialyser is a two-compartment structure composed of repeated stack of cationic membrane and bipolar membrane; both sides of membrane stack are electrified with direct current whose density is 80 A/m$^2$, and lactic acid sodium is decomposed into lactic acid and sodium hydroxide. Among them, sodium hydroxide coming from cationic compartment is reintroduced into fermentation unit for regulating pH, and lactic acid solution with mass percentage concentration of 6% comes from bipolar membrane compartment.

(6) Lactic acid solution issuing from bipolar membrane compartment is fed into vacuum distillation unit, and dehydrated to obtain lactic acid product with mass percentage concentration of 85%, whose quality meet the standard of GB2023-2003.

The invention claimed is:

1. A cleaning process of producing lactic acid, comprising:
preparing a saccharification liquid through saccharated materials;
fermenting, by a fermentation unit, with nutritive materials and a lactic acid bacteria, forming a fermentation broth;
adjusting the pH using a liquid alkali;
pumping the fermentation broth into a ceramic membrane when a mass percentage concentration of a sugar content reaches a designated amount;
filtrating the fermentation broth with the ceramic membrane, wherein an intercepted retentate forms an interception liquid;
reintroducing the interception liquid into the fermentation unit for recycling;
feeding a permeate from the ceramic membrane to a nanofiltration unit to be decoloured and purified, wherein an intercepted nanofiltration retentate forms a concentrated solution;
introducing the concentrated solution into a sterilization system wherein the concentrated solution from the nanofiltration unit and a fermentation unit cleaning liquid are filtrated by a sterilization system ceramic membrane to remove hybrid bacteria before reintroducing the concentrated solution into the fermentation unit for recycling;
subjecting the permeate from the nanofiltration unit to a bipolar electrodialysis system to prepare lactic acid, and the liquid alkali produced at the same time is reintroduced into the fermentation tank for recycling; and
concentrating the lactic acid by using vacuum distillation.

2. The process according to claim 1, wherein said saccharated materials are at least one of corn, wheat, yam, potato, molasses and plant fiber; said prepared saccharification liquid is an aqueous solution with a mass percentage concentration of glucose being 10~30%.

3. The process according to claim 1, wherein said nutritive materials are at least one of soybean meal hydrolysate, bran or corn steep liquor; the addition amount of nutritive materials (dry weight) is 0.1~10% of a total mass of saccharification liquid; said lactic acid bacteria is *L. delbrueckii*, and the lactic acid bacteria addition amount is 5~20% of a total volume of saccharification liquid, wherein a fermentation temperature is 45~60° C. and pH is 5~7.

4. The process according to claim 1, wherein said liquid alkali refers to an aqueous solution containing a hydrate with at least one of a monovalent cation, sodium hydroxide, potassium hydroxide and ammonium hydroxide, wherein a mass percentage concentration of liquid alkali is 5%~30%.

5. The process according to claim 1, wherein the pore size of the ceramic membrane is 5 nm~15 μm.

6. The process according to claim 5, wherein a the fermentation broth is filtrated with said ceramic membrane, with an operation pressure being 0.01~0.5 MPa and a flow velocity of membrane surface being 0.01~5 m/s, wherein the permeate from ceramic membrane is fed to said nanofiltration unit for decoloring and purification, with the operating pressure being 0.5~2.5 MPa.

7. The process according to claim 1, wherein said sterilization system ceramic membrane has a pore size of 20 nm~100 nm, a flow velocity of 0.01~3 m/s and a cycle of concentration is—8~10.

8. The process according to claim 1, wherein an operating current density of said bipolar electrodialysis system is 30~300 A/m$^2$, and a mass percentage concentration of lactate salt in the permeate from the nanofiltration unit introduced into the bipolar electrodialysis system is 10~40%.

9. The process according to claim 1, wherein the bipolar electrodialyser employed in the said bipolar electrodialysis process is a composite membrane stack structure of two or three compartments.

* * * * *

UNITED STATES PATENT AND TRADEMARK OFFICE
CERTIFICATE OF CORRECTION

PATENT NO. : 8,545,685 B2  
APPLICATION NO. : 13/127307  
DATED : October 1, 2013  
INVENTOR(S) : Xu et al.

It is certified that error appears in the above-identified patent and that said Letters Patent is hereby corrected as shown below:

In the Drawings

Drawing Sheet 1

Insert --Figure 1--

In the Specifications

Column 2

Line 22, after "be" delete "decoloured" and insert --decolored--

Line 52, after "for" delete "decolour" and insert --decolor--

Column 3

Line 16, after "is" delete "0.1~40%" and insert --0.1~10%--

In the Claims

Column 7, Claim 7

Line 43, after "be" delete "decoloured" and insert --decolored--

Column 8, Claim 6

Line 28, after "wherein" delete "a"

Signed and Sealed this  
Seventeenth Day of December, 2013

Margaret A. Focarino  
*Commissioner for Patents of the United States Patent and Trademark Office*